United States Patent [19]

Mich et al.

[11] Patent Number: 4,692,454

[45] Date of Patent: Sep. 8, 1987

[54] OPTHALMIC USE OF QUINOLONE ANTIBIOTICS

[75] Inventors: Thomas F. Mich; Carl L. Heifetz, both of Ann Arbor, Mich.

[73] Assignee: Warner-Lambert Company, Morris Plains, N.J.

[21] Appl. No.: 825,007

[22] Filed: Feb. 3, 1986

[51] Int. Cl.⁴ ............................................. A61K 31/47
[52] U.S. Cl. .................................... 514/312; 514/912
[58] Field of Search ......................... 514/300, 312, 912

[56] References Cited

U.S. PATENT DOCUMENTS

| | | | |
|---|---|---|---|
| 3,753,993 | 8/1973 | Lesher et al. | 546/156 |
| 3,907,808 | 9/1975 | Lesher et al. | 546/156 |
| 3,963,736 | 6/1976 | Nakagone et al. | 546/123 |
| 4,146,719 | 3/1979 | Irikura | 546/156 |
| 4,284,629 | 8/1981 | Grohe et al. | 546/318 |
| 4,341,784 | 7/1982 | Matsumoto et al. | 546/123 |
| 4,382,892 | 5/1983 | Hayakawa et al. | 544/101 |
| 4,382,937 | 5/1983 | Matsumoto et al. | 546/123 |
| 4,398,029 | 8/1983 | Irikura et al. | 546/156 |
| 4,429,127 | 1/1984 | Irikura et al. | 546/156 |
| 4,448,962 | 5/1984 | Irikura et al. | 546/156 |
| 4,499,091 | 2/1985 | Weatland et al. | 546/156 |
| 4,551,456 | 11/1985 | Katz | 514/254 |
| 4,556,658 | 12/1985 | Grohe et al. | 514/254 |
| 4,604,401 | 8/1986 | Mich et al. | 514/312 |

FOREIGN PATENT DOCUMENTS

| | | | |
|---|---|---|---|
| 0049355 | 8/1981 | European Pat. Off. | 546/314 |
| 0126355 | 5/1984 | European Pat. Off. | 546/314 |
| 3318145 | 11/1984 | Fed. Rep. of Germany | 546/156 |
| 1086476 | 7/1976 | Japan | 546/156 |
| 7149286 | 9/1982 | Japan | 544/101 |
| 8072589 | 4/1983 | Japan | 544/101 |
| 61-126082 | 6/1986 | Japan | 514/300 |

OTHER PUBLICATIONS

Koga et al., J. Med. Chem. 23, pp. 1358–1363, (1980)-Structure Activity Relationships of Antibacterial-4-oxoquinolines.

Rufer et al., Eur. J. Med. Chem.-Chimica Therapeutica-Jan.-Feb. (1977), vol. 12, (1), pp. 27–29, "Chinoloncarbon sawren V".

Chem. Abst. 101:72740(t), (1984)-Culbertson et al.
Chem. Abst. 104:34013n, (1986)-Culbertson et al.
Chem. Abst. 104:129777d, (1986)-Domagala et al.

*Primary Examiner*—Douglas W. Robinson
*Attorney, Agent, or Firm*—Ronald A. Daignault

[57] ABSTRACT

Certain quinolone and naphthyridine antibiotics are useful for treating ocular infections by topical administration.

10 Claims, No Drawings

OPTHALMIC USE OF QUINOLONE ANTIBIOTICS

BACKGROUND OF THE INVENTION

The quinolone and naphthyridine compounds of the present invention are known antibacterial agents and are active against a broad spectrum of gram-positive and gram-negative organisms as described in European Patent Publication No. 106,489.

The majority of bacterial ocular infections are caused by gram-positive bacteria. Because the above quinolone and naphthyridine compounds have remarkable activity against such bacteria, they were selected as excellent candidates in treating such infections.

SUMMARY OF THE INVENTION

The present invention relates to the discovery that these broad spectrum antibiotics are compatible with ocular tissue and that therapeutic levels are detected in various ocular tissues and fluids after topical administration and are thus useful for treating a wide variety of bacterial ocular infections by topical administration.

In addition, compositions containing these antibacterial agents have veterinary use, e.g., in the treatment of red eye in cattle and other animals.

Furthermore, compositions containing the subject agents are for a variety of disinfectant applications, e.g., as an active component in preparations for cleaning and/or disinfecting contact lenses.

Accordingly, the present invention has for its object a method of treating bacterial ocular infections by topical administration of an antibacterially effective amount of a compound of the Formula I

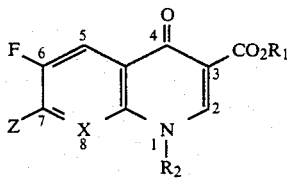

wherein Z is

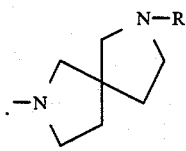

in which n is zero or one and $R_3$ is hydrogen, methyl, ethyl, 1- or 2-propyl; X is CH, CF, or N; $R^1$ is hydrogen or alkyl having from one to six carbon atoms; $R^2$ is alkyl having from one to four carbon atoms, vinyl, haloalkyl or hydroxyalkyl having from two to four carbon atoms, or cycloalkyl having three to six carbon atoms; or an ophthalmologically acceptable acid addition salt or base salt thereof in admixture with a nontoxic pharmaceutical organic or inorganic carrier.

It has as a further object the provision of compositions containing antibacterially effective amounts of the compounds of Formula I.

DETAILED DESCRIPTION OF THE EMBODIMENTS

As preferred active ingredients for the compositions of the present invention are those of Formula I wherein $R_1$ is hydrogen or an ophthalmologically acceptable base salt such as a metal or amine salt, e.g., sodium or potassium salts.

Other preferred active ingredients are those of Formula I wherein $R_2$ is ethyl or cyclopropyl and X is CF or N, or an ophthalmologically acceptable acid addition or base salt thereof.

Preferred ophthalmologically acceptable acid addition salts are those from mineral or organic acids, e.g., hydrochloric, maleic, pamoic, or the like.

Particularly preferred active ingredients are the following:

7-[3-aminomethyl)-1-pyrrolidinyl]-1-ethyl-6-fluoro-1,4-dihydro-4-oxo-1,8-naphthyridine-3-carboxyic acid;

7-[3-(aminomethyl)-1-pyrrolidinyl]-1-ethyl-6,8-difluoro-1,4-dihydro-4-oxo-3-quinolinecarboxylic acid;

1-ethyl-7-[3-[(ethylamino)methyl]-1-pyrrolidinyl]-6-fluoro-1,4-dihydro-4-oxo-1,8-naphthyridine-3-carboxylic acid;

1-ethyl-7-[3-[(ethylamino)methyl]-1-pyrrolidinyl]-6,8-difluoro-1,4-dihydro-4-oxo-3-quinolinecarboxyic acid;

1-ethyl-6-fluoro-1,4-dihydro-7-[[(1-methylethyl)amino]methyl]-1-pyrrolidinyl]-4-oxo-1,8-naphthyridine-3-carboxylic acid;

1-ethyl-7-[3-[[(1-methylethyl)amino]methyl]-1-pyrrolidinyl]-6,8-difluoro-1,4-dihydro-4-oxo-3-quinolinecarboxylic acid;

1-ethyl-6-fluoro-1,4-dihydro-7-(7-methyl-2,7-diazaspiro[4.4]non-2-yl)-4-oxo-1,8-naphthyridine-3-carboxylic acid;

1-ethyl-6,8-difluoro-1,4-dihydro-7-(7-ethyl-2,7-diazaspiro[4.4]non-2-yl)-4-oxo-3-quinolinecarboxylic acid;

1-ethyl-6,8-difluoro-1,4-dihydro-7-(7-methyl-2,7-diazaspiro[4.4]non-2-yl)-4-oxo-3-quinolinecarboxylic acid;

7-(3-amino-1-pyrrolidinyl)-1-ethyl-6,8-difluoro-1,4-dihydro-4-oxo-3-quinolinecarboxylic acid;

7-[3-(aminomethyl)-1-pyrrolidinyl]-1-cyclopropyl-6,8-difluoro-1,4-dihydro-4-oxo-3-quinolinecarboxylic acid;

1-cyclopropyl-7-[3-[(ethylamino)methyl]-1-pyrrolidinyl]-6,8-difluoro-1,4-dihydro-4-oxo-3-quinolinecarboxylic acid;

7-[3-amino-1-pyrrolidinyl]-1-cyclopropyl-6,8-difluoro-1,4-dihydro-4-oxo-3-quinolinecarboxylic acid;

1-cyclopropyl-7-[3-[(methylamino)methyl]-1-pyrrolidinyl]-6,8-difluoro-1,4-dihydro-4-dihydro-4-oxo-3-quinolinecarboxylic acid;

1-cyclopropyl-7-[3-(ethylamino)-1-pyrrolidinyl]-6,8-difluoro-1,4-dihydro-4-oxo-3-quinolinecarboxylic acid;

1-cyclopropyl-6,8-difluoro-1,4-dihydro-7-[3-[[(1-methylethyl)amino]methyl]-1-pyrrolidinyl]-4-oxo-3-quinolinecarboxylic acid;

7-[3-(aminomethyl)-1-pyrrolidinyl]-1-cyclopropyl-1,4-dihydro-6-fluoro-4-oxo-1,8-naphthyridine-3-carboxylic acid;

1-cyclopropyl-7-[3-[(ethylamino)methyl]-1-pyrrolidinyl]-1,4-dihydro-6-fluoro-4-oxo-1,8-naphthyridine-3-carboxylic acid;

7-[3-amino-1-pyrrolidinyl]-1-cyclopropyl-1,4-dihydro-6-fluoro-4-oxo-1,8-naphthyridine-3-carboxylic acid;

or the ophthalmologically acceptable acid addition or base salts thereof.

The active ingredients of Formula I may be prepared by the methods described in European Patent Publication No. 106,489 or in copending U.S. application Ser. No. 692,820.

Formulations of these compounds may contain from about 0.003 to 3% and especially 0.15 to 0.6% of medicament although higher or lower dosages can be employed. As a unit dosage form between 0.015 to 1.5 mg, preferably 0.05 to 1.0 mg, and especially 0.1 to 0.3 mg of the compound is generally applied to the human eye, and can be administered as frequently as necessary.

These hereinbefore described dosage values are believed accurate for human patients and are based on the known and presently understood pharmacology of the compounds, and the action of other similar entities in the human eye. They reflect the best mode known. As with all medications, dosage requirements are variable and must be individualized on the basis of the disease and the response of the patient.

In the pharmaceutical preparation the active compound conveniently is admixed with a nontoxic pharmaceutical organic carrier, or with a nontoxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethyl-cellulose, polyvinylpyrrolidone, isopropyl myristate and other conventionally employed acceptable carriers. The ophthalmological preparation may also contain nontoxic auxiliary substances such as emulsifying, preserving, wetting agents, bodying agents and the like, as for example, polyethylene glycols 200, 300, 400, and 600, carbowaxes 1,000, 1,500, 4,000, 6,000, and 10,000, other antibacterial components such as quaternary ammonium compounds, phenylmercuric salts known to have cold sterilizing properties and which are noninjurious in use, thimerosal, methyl and propyl paraben, benzyl alcohol, phenylethanol, buffering ingredients such as sodium chloride, sodium borate, sodium acetate, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a solid insert.

While many patients find liquid medication to be entirely satisfactory, others may prefer a solid medicament that it topically applied to the eye, for example, a solid dosage form that is suitable for insertion into the cul-de-sac. To this end of the antibiotic can be included with a nonbioerodible insert, i.e., one which after dispensing the drug remains essentially intact, or a bioerodible insert, i.e., one that either is soluble in lacrimal fluids, or otherwise disintegrates. While the insert employed is not critical and those disclosed in U.S. Pat. No. 3,630,200 Higuchi; No. 3,811,444 Heller, et al; No. 4,177,256 Michaels, et al; No. 3,868,445 Ryde, et al; No. 3,845,201 Haddad; No. 3,981,303 Higuchi; and No. 3,867,519 Michaels, are satisfactory; in general, however, the inserts described below are found preferable.

For example, one may use a solid water soluble polymer as the carrier for the medicament. The polymer used to form the insert may be any water soluble nontoxic polymer, for example, cellulose derivatives such as methylcellulose, sodium carboxymethyl cellulose, or a hydroxy lower alkyl cellulose such as hydroxyethyl cellulose, hydroxypropyl cellulose, hydroxypropylmethyl cellulose and the like; acrylates such as polyacrylic acid salts, ethyl acrylates, polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, and mixtures of said polymer.

The ophthalmic formulation may also be in the form of a clear physiologically-acceptable liquid which forms a semi-solid "gel" at human body temperatures. Polymers having these properties are tetra substituted derivatives of ethylene diamine (poloxamine, w=2 in Formula I), propylene diamine (w=3), butylene diamine (w=4), pentylene diamine (w=5) or hexylene diamine (w=6). The substituents are block copolymers of poly(oxypropylene) and poly(oxyethylene) of various chain lengths and ratios x to y in the general formula of the polymer shown below $$H(OC_2H_4)_y(OC_3H_6)_x \diagdown \diagup (C_3H_6O)_x(C_2H_4O)_yH$$
$$N-(CH_2)_n-N$$
$$H(OC_2H_4)_y(OC_3H_6)_x \diagup \diagdown (C_3H_6O)_x(C_2H_4O)_yH$$

wherein w is an integer from two through six.

A typical polymer system would contain a polymer containing approximately 40 to 80% poly(oxypropylene). The total molecular weight of the polymer used is at a minimum about 7,000 and can go as high as 50,000 but preferably in the range of 7,000 to 30,000, and x and y are any integers within the above constraints. Preferred polymers are those of the formula above where w=2, namely the poloxamine polymer.

The aqueous drug delivery vehicle would contain from 10% to 50% by weight of the entire vehicle as polymer described above. The aqueous drug delivery vehicle would also contain the drug of therapeutic agent in addition to various additives such as acids or bases to adjust the pH of the composition, buffers to maintain the pH, preservatives to control bacterial contamination, other additives to provide for drug solubility and stability and formulation performance with purified water making up the remainder of the drug delivery vehicle.

The ophthalmic formulations may also be in form of stable purilamellar vesicles which comprise the antibiotic active ingredient encapsulated with liposomes as described in U.S. Pat. No. 4,552,803.

| Formulation of 0.3% Solution | |
|---|---|
| Ingredient | mg/ml |
| EXAMPLE 1 | |
| 1-Ethyl-7-[3-(ethylamino)methyl]-1-pyrrolidinyl]-6,8-difluoro-1,4-dihydro-4-oxo-3-quinolinecarboxylic acid | 3.0 |

| -continued | |
| --- | --- |
| Formulation of 0.3% Solution | |
| Ingredient | mg/ml |
| Sodium acetate 3H$_2$O | 2.72 |
| Benzalkonium chloride | 0.11 |
| Ethylenediamine tetraacetic acid, disodium salt | 0.10 |
| Sodium chloride | 7.42 |
| Hydrochloric acid to pH | 5.2 |
| Water q.s. | |
| EXAMPLE 2 | |
| 1-Cyclopropyl-7-[3-(ethylamino)methyl]-1-pyrrolidinyl]-6,8-difluoro-1,4-dihydro-4-oxo-3-quinolinecarboxylic acid hydrochloride | 3.0 |
| Petrolatum q.s. ad. | 1.0 g |
| EXAMPLE 3 | |
| 7-[3-Amino-1-pyrrolidinyl]-1-cyclopropyl-6,8-difluoro-1,4-dihydro-4-oxo-3-quinolinecarboxylic acid hydrochloride | 1.0 |
| Hydroxypropylcellulose q.s. | 12.0 |

Ophthalmic inserts are manufactured from compression molded films which are prepared on a Carver Press by subjecting the powdered mixture of the above ingredients to a compressional force of 12,000 pounds (gauge) at 300° F. for one to four minutes. The film is cooled under pressure by having cold water circuits in the platen. Ophthalmic inserts are then individually cut from thwe film with a rod-shaped punch. Each insert is placed into a vial, which is then placed in a humidity cabinet (88% R.H. at 30° C.) for two to four days. After removal from the humidity cabinet, the vial containing the hydrate insert are then autoclaved at 250° F. for 0.5 hour.

Reasonable variations, such as those which would occur to a skilled artisan, can be made herein without departing from the scope of the invention.

We claim:

1. A method of treating ocular bacterial infections which comprises topical ocular administration to an infected eye of an antibacterially effective amount of a compound of the formula

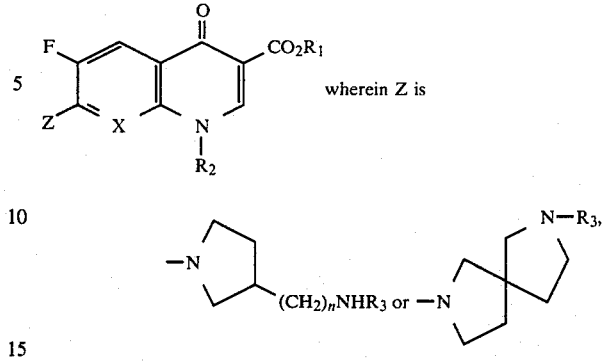

wherein Z is in which n is zero or one and $R_3$ is hydrogen, methyl, ethyl, 1- or 2-propyl; X is CH, or CF; $R_1$ is hydrogen or alkyl having from one to six carbon atoms; $R_2$ is alkyl having from one to four carbon atoms, vinyl, haloalkyl, hydroxyalkyl having from two to four carbon atoms, or cycloalkyl having three to six carbon atoms, or an ophthalmologically acceptable acid addition or base salt thereof in admixture with a nontoxic pharmaceutical organic or inorganic carrier.

2. The method of claim 1 wherein X is CF; $R_1$ is hydrogen; $R_2$ is ethyl or cyclopropyl, or an ophthalmologically acceptable acid addition or base salt thereof.

3. The method of claim 2 wherein the compound is 7-[3-(aminomethyl)-1-pyrrolidinyl]-1-ethyl-6,8-difluoro-1,4-dihydro-4-oxo-3-quinoline carboxylic acid.

4. The method of claim 2 wherein the compound is 1-ethyl-7-[3-(ethylamino)methyl]-1-pyrrolidinyl-6,8-difluoro-1,4-dihydro-4-oxo-3-quinolinecarboxylic acid.

5. The method of claim 2 wherein the compound is 1-ethyl-6,8-difluoro-1,4-dihydro-7-(7-methyl-2,7-diazaspiro[4.4]non-2-yl-4-oxo-3-quinolinecarboxylic acid.

6. The method of claim 2 wherein the compound is 7-[3-(aminomethyl)-1-pyrrolidinyl]-1-cyclopropyl-6,8-difluoro-1,4-dihydro-4-oxo-3-quinoline-carboxylic acid.

7. The method of claim 2 wherein the compound is 1-cyclopropyl-7-[3-[(ethylamino)-methyl]-1-pyrrolidinyl]-6,8-difluoro-1,4-dihydro-4-oxo-3-quinolinecarboxylic acid.

8. The method of claim 2 wherein the compound is 7-[3-amino-1-pyrrolidinyl]-1-cyclopropyl-6,8-difluoro-1,4-dihydro-4-oxo-3-quinolinecarboxylic acid.

9. The method of claim 2 wherein the compound is 1-cyclopropyl-7-[3-[methylamino)methyl]-1-pyrroidinyl]-6,8-difluoro-1,4-dihydro-4-oxo-3-quinolinecarboxylic acid.

10. The method of claim 2 wherein the compound is 1-cyclopropyl-7-[3-ethylamino)-1-pyrroidinyl]-6,8-difluoro-1,4-dihydro-4-oxo-3-quinolinecarboxylic acid.

* * * * *

UNITED STATES PATENT AND TRADEMARK OFFICE
CERTIFICATE OF CORRECTION

PATENT NO. : 4,692,454
DATED : September 8, 1987
INVENTOR(S) : Thomas F. Mich, Carl L. Heifetz It is certified that error appears in the above—identified patent and that said Letters Patent is hereby corrected as shown below:

Title Page, No. 54, 1st line   Delete "Opthalmic" and substitute --Ophthalmic--.

Col. 1, line 2   Delete "Opthalmic" and substitute --Ophthalmic--.

Col. 2, line 29   Delete "7-[[" and substitute -- 7-[3-[[ --.

Col. 2, line 53   Delete "-4-dihydro" and substitute -- -1,4-dihydro --.

Col. 3, line 58   Delete "it" and substitute --is--.

Col. 4, line 34   Delete "$(CH_2)_n$" and substitute --$(CH_2)_w$--.

Col. 5, line 37   Delete "thwe" and substitute --the--.

Col. 5, line 42   Delete "are" and substitute --is--.

Col. 6, lines 49-50   Delete "3-[methylamino)methyl]-1-pyrroidinyl" and substitute -- 3-[(methylamino)methyl]-1-pyrrolidinyl --.

Col. 6, line 53   Delete "3-et" and substitute -- 3-(ethylamin--

Signed and Sealed this

Twenty-ninth Day of March, 1988

*Attest:*

DONALD J. QUIGG

*Attesting Officer*   *Commissioner of Patents and Trademarks*